United States Patent [19]

Zito et al.

[11] Patent Number: 4,525,455
[45] Date of Patent: Jun. 25, 1985

[54] **METHOD FOR PREPARING A CELL FREE HOMOGENATE OF *CHRYSANTHEMUM CINERARIAEFOLIUM* (TREV.) BOCC. CONTAINING ENZYMES AND METHODS OF USE**

[75] Inventors: Santo W. Zito; E. John Staba, both of Minneapolis, Minn.

[73] Assignee: Regents of the University of Minnesota, Minneapolis, Minn.

[21] Appl. No.: 489,957

[22] Filed: Apr. 29, 1983

[51] Int. Cl.³ .......................... C12P 7/62; C12P 7/02; C12N 9/14

[52] U.S. Cl. .................................. 435/135; 435/155; 435/188; 435/195; 435/196; 435/178

[58] Field of Search ............... 435/131, 135, 136, 148, 435/149, 155, 188, 195, 196, 178

[56] References Cited

U.S. PATENT DOCUMENTS 3,952,047  4/1976  Moore et al.
4,281,171  7/1981  Sims.
4,284,966  2/1981  Demain et al.
4,307,192  12/1981  Demain et al.

FOREIGN PATENT DOCUMENTS 0022434  1/1981  European Pat. Off.

OTHER PUBLICATIONS

Kreuz et al.–Chem. Abst., vol. 96, (1982), p. 82780y.
Chem. Abstract: Isolation of D-Ribulose 1, 5-Diphosphate from Ribose 5-Phosphate and Adenosine Triphosphate, vol. 95, p. 398 (1981).
R. Bourne & M. Rosenthal, *Pyrethrum Post*, vol. 13(4), pp. 127–131.
W. Loomis & J. Battaile, *Phytochemistry*, vol. 5, pp. 423–438 (1966).
P. Heinstein, et al., *J. of Biol. Chem.*, vol. 245, No. 18, pp. 4658–4665 (1970).
P. Benveniste, *Phytochemistry*, vol. 9, pp. 1073–1082 (1970).
J. Casida (Editor), *Pyrethrum—The Natural Insecticide*, (Academic Press 1973), pp. 77–79 and 106–108.
P. Heinstein, et al., *Planta Medica*, vol. 37, pp. 349–357 (1979).

*Primary Examiner*—Sam Rosen
*Attorney, Agent, or Firm*—Dorsey & Whitney

[57] ABSTRACT

A method is disclosed for preparing a cell free homogenate from Chrysanthemum species and Tagetes species of the family Compositae which contains the bioactive enzyme(s) and cofactor(s) of the pyrethrum pathway. A method is also disclosed for preparing a cell free matrix containing these bioactive enzyme(s) and cofactor(s). The homogenate and matrix will convert mevalonic acid, labeled mevalonic acid, isopentenyl pyrophosphate or labeled isopentenyl pyrophosphate into pyrethrins, labeled pyrethrins, chrysanthemyl alcohol or labeled chrysanthemyl alcohol.

60 Claims, 12 Drawing Figures

3,5 DINITROBENZOATE ESTER OF
CHRYSANTHEMYL ALCOHOL

*Fig 8*

INCORPORATION OF RADIOACTIVITY OF 2-$C^{14}$
MEVALONIC ACID INTO PYRETHRINS USING CFS

PYRETHRINS II      PYRETHRINS I

*Fig 9*

INCORPORATION OF RADIOACTIVITY INTO CHRYSANTHEMYL
ALCOHOL BY IMMOBILIZED INCUBATION

CHRYSANTHEMYL
ALCOHOL

METHOD FOR PREPARING A CELL FREE HOMOGENATE OF CHRYSANTHEMUM CINERARIAEFOLIUM (TREV.) BOCC. CONTAINING ENZYMES AND METHODS OF USE

BACKGROUND OF THE INVENTION

1. Field of the Invention

This invention relates to a method for preparing a cell free homogenate containing bioactive enzyme(s) and cofactor(s) of the pyrethrin pathway of *Chrysanthemum cinerariaefolium* (Trev.) Bocc. This cell free homogenate will convert mevalonic acid or isopentenyl pyrophospate into pyrethrins and chrysanthemyl alcohol.

2. Description of the Prior Art

Pyrethrins are a collection of six structurally related insecticidal esters found in *Chrysanthemum cinerariaefolium* (Trev.) Bocc. Pyrethrins I refers herein to the chrysanthemates of pyrethrin, cinerin, and jasmolin, while pyrethrins II refers herein to the pyrethrates of pyrethrin, cinerin, and jasmolin. (Cf. R. Bourne & M. Rosenthal, "(Summary of Attempts to Obtain Radioactively Labeled Pyrethrum Extract," *PYRETHRUM Post*, Vol. 13 (4), pp. 127-131, at 128). These compounds are effective, non-persistent insecticides used commercially in many applications, particularly in pediculocides and in preparation for insect control in industry kitchens. Pyrethrins are produced commercially by harvesting the flower heads of plants grown on farms throughout the world but particularly in Kenya and Ecuador.

Radiolabeled pyrethrins are an important tool for the evaluation and elucidation of the metabolic fate of pyrethrins in animals and insects. Absorption of labeled pyrethrin preparations through the skin or mucosal tissue of animals can assist in determining the safety of the use of such pyrethrin preparations. Labeled pyrethrins can be used to further our understanding of the fate of pyrethrins in the metabolism of target insects.

Prior art attempts to produce radiolabeled pyrethrins include the following. In John E. Casida (Ed.), *PYRETHRUM—THE NATURAL INSECTICIDE* (Academic Press 1973), at pages 77-79 and 106-108, several methods for radiolabeling pyrethrins are set forth. Pyrethrum plants were grown in $^{14}CO_2$ or mevalonate, acetate, or methionine containing ($^{14}C$). In another method, chrysanthemic acid containing $^{14}C$ was synthesized and used in turn to synthesize radiolabeled pyrethrins. In yet another method, pyrethrolone was tritiated and upon esterfication yielded tritiated pyrethrins. In Bourne & Rosenthal, supra, the above method for tritiating pyrethrolone is discussed in addition to methods for labeling pyrethrins with $^{14}C$. These methods are generally disparaged by Bourne & Rosenthal.

Cell free homogenates have been used in other fields of art to study biochemical pathways. Enzymes liberated in a cell free homogenate may be isolated and purified for subsequent use by batch or immobilized techniques as a catalyst in a desired reaction. L-amino acids are produced by the enzyme aminoacylase from *Aspergillus oryzae* immobilized by binding to DEAE-Sephadex. This method of producing L-amino acids is carried out by Tanabe Seiyaku Co., Japan. A cell free homogenate prepared from *Gossypium hirsutum* biosynthesizes gossypol from cis-cis farnesyl pyrophosphate. (P. Heinstein, et al., *J. BIOL. CHEM.*, Vol. 245, No. 18, p. 4658 (1970)). A cell free homogenate prepared from *Nicotiana tabacum* tissue cultures biosynthesizes squalene from mevalonic acid. (P. Benveniste, et al., *PHYTOCHEM* Vol. 9, p. 1073 (1969)). A cell free homogenate from *Catharanthus roseus* cell suspensions synthesizes the heteroyohimbine alkaloids ajmalicine, 19-epiajmalicine and tetrahydroalstonine from geissoschizine. (Stockigt, et al., *FEDS LETTERS*, Vol. 70, p. 167 (1976); Stockigt, et al., *PLANTA MEDICA*, Vol. 37 p. 349 (1980)). U.S. Pat. Nos. 4,248,966 and 4,307,192, issued to Demain et al., issued Feb. 3, 1981 and Dec. 22, 1981 respectively, show the use of cell free homogenates for the synthesis of isopenicillin derivatives.

SUMMARY OF THE INVENTION

In accordance with the invention, it has been discovered that certain cell free homogenates prepared from *Chrysanthemum cinerariaefolium* (Trev.) Bocc. contain the bioactive enzyme(s) and cofactor(s) of the pyrethrin pathway of the plant. Such cell free homogenates may also be prepared from other pyrethrin producing Chrysanthemum species or Tagetes species of the family Compositae. These cell free homogenates will convert mevalonic acid or isopentenyl pyrophosphate into pyrethrins. A cell free homogenate containing such bioactive enzyme(s) and cofactor(s) is prepared by homogenizing fresh plant material by mechanical means such as mortar-pestle, homogenizers, or blenders, or by non-mechanical means. The plant material is homogenized in the presence of a hydrogen bonding inhibitor and a stabilizing solution. The hydrogen bonding inhibitor is used in an amount effective to competitively inhibit the hydrogen bonding of the bioactive enzyme(s) and cofactor(s) by plant phenolics. The stabilizing solution comprises a buffer with a pH in the range of about 6-8.5 and a thiol-reducing agent in an amount effective to competitively inhibit oxidation of bioactive enzyme(s) and cofactor(s) containing sulfhydryl groups and/or to competitively inhibit oxidation or covalent bonding of bioactive enzyme(s) and cofactor(s) by plant quinones.

Mevalonic acid or isopentenyl pyrophosphate upon incubation with a cell free homogenate prepared according to the above method will be converted into pyrethrins. Similarly, labeled mevalonic acid or labeled isopentenyl pyrophosphate will be converted into labeled pyrethrins. Chrysanthemyl alcohol and its labeled analog are prepared by hydrolyzing the chrysanthemyl alcohol pyrophosphate formed by the conversion of mevalonic acid or isopentenyl pyrophosphate by the cell free homogenate.

A cell free homogenate prepared according to the above method may be used as a reagent to convert mevalonic acid or isopentenyl pyrophosphate to pyrethrins or pyrethrin intermediates by batch procedures. The cell free homogenate may also be used as a reagent for the production of labeled pyrethrins or labeled pyrethrin intermediates where labeled mevalonic acid or isopentenyl pyrophosphate is utilized. The enzyme(s) and cofactor(s) in the cell free homogenate may be immobilized by to DEAE-Sephadex or calcium alginate, for example, and used as a reagent catalyst for the production of pyrethrins. Finally, the cell free homogenate can be used as a source of particular enzymes which are useful for preparing pyrethrin intermediates for the semi-synthesis of pyrethroids.

DESCRIPTION OF THE PREFERRED EMBODIMENT

1. Preparation of Plant Material

Young and unopened flower buds and/or young and folded leaves (approximately 1–10 mm long) of *Chrysanthemum cinerariaefolium* (Trev.) Bocc. (syn: *Tanacetum cinerarifolium* (Trev.) and *Pyrethrum cinerarifolium* (Schultz Bip.)) and related Compositae plants may be used as plant material. Suspension tissue cultures as well as shoot and plantlet cultures grown in liquid or in solid matrix medium may also be used as plant material. These tissue cultures may be derived according to the following methods.

Tissue cultures are derived from sterile germination of *Chrysanthemum cinerariaefolium* (Trev.) Bocc. seeds and plants from related Compositae. Shoot cultures may be established from these seedlings on liquid RT medium containing 3 ppm benzyladenine. The seedlings, when grown on Murashige-Skoog revised tobacco medium (RT), 1% agar, and 1 ppm 2,4-dichlorophenoxyacetic acid (2, 4D), develop callus within 3–4 weeks. The callus tissues may be transferred to liquid RT medium containing 0.1 ppm 2, 4D for establishing suspension cultures.

2. Preparation of Cell Free Homogenate

Fresh plant material is mixed with an equal mass (i.e., grams) of powdered insoluble polyvinylpyrrolidone in a glass mortar and pestle. Stabilizing solution, comprising 0.1M 2(N-morpholino) ethane sulfonic acid (pH 7.0) ("MES"), 0.5M sucrose, 0.1M sodium ascorbate, and 0.1M β-mercaptoethanol is added in a ratio of 5 ml per gram of fresh plant material. Grinding in the mortar and pestle is continued until a smooth, free flowing paste is achieved. Equally active cell free homogenates can be prepared using blenders or homogenizers. The free flowing paste is centrifuged at 7000 rpm in a clinical table top centrifuge for 10 minutes. The supernatant is recovered as the cell free homogenate.

The cell free homogenate is stable for at least 4 weeks when stored in a closed glass container at 4° C. Boiling or freezing of the cell free homogenate results in loss of activity.

As an alternative to powdered insoluble polyvinylpyrrolidone, soluble polyvinylpyrrolidone may be used. As further alternatives, hydrogen bonding inhibitors in amounts effective to competitively inhibit hydrogen bonding of the bioactive enzyme(s) and cofactor(s) by plant phenolics, such as nylon, carotene, collagen, polyamides, polyacrylamides, casein, arylhalides, or ethers may be used.

The preferred stabilizing solution is added in a ratio of 5 ml per gram of fresh weight of plant material which is equivalent to adding 0.5 mmole MES, 2.5 mmole sucrose, 0.5 mmole sodium ascorbate, and 0.5 mmole β-mercaptoethanol per gram of plant material. As an alternative, these preferred quantities of the foregoing compounds may be used in a ratio other than the preferred 5 ml per gram fresh weight of plant material.

As an alternative to 0.1M MES buffer, 0.1M 2(N-morpholino) propane sulfonic acid, 0.1M phosphate buffer, or 0.1M Tris buffer may be used. As an alternative to 0.1M β-mercaptoethanol, a thiol-reducing agent in an amount effective to competitively inhibit oxidation of bioactive enzyme(s) and cofactor(s) containing sulfhydryl groups and/or to competitively inhibit oxidation of covalent bonding of bioactive enzyme(s) and cofactor(s) by plant quinones, such as other mercaptans like dithiothreitol, dithioerythritol, or glutathione may be used. As an alternative to sucrose, other osmoticum reagents which tend to preserve the integrity of cellular compartments may be used. Anti-oxidants which tend to reduce oxidation of the bioactive enzyme(s) and cofactor(s) may be used in place of sodium ascorbate.

Figure 1:
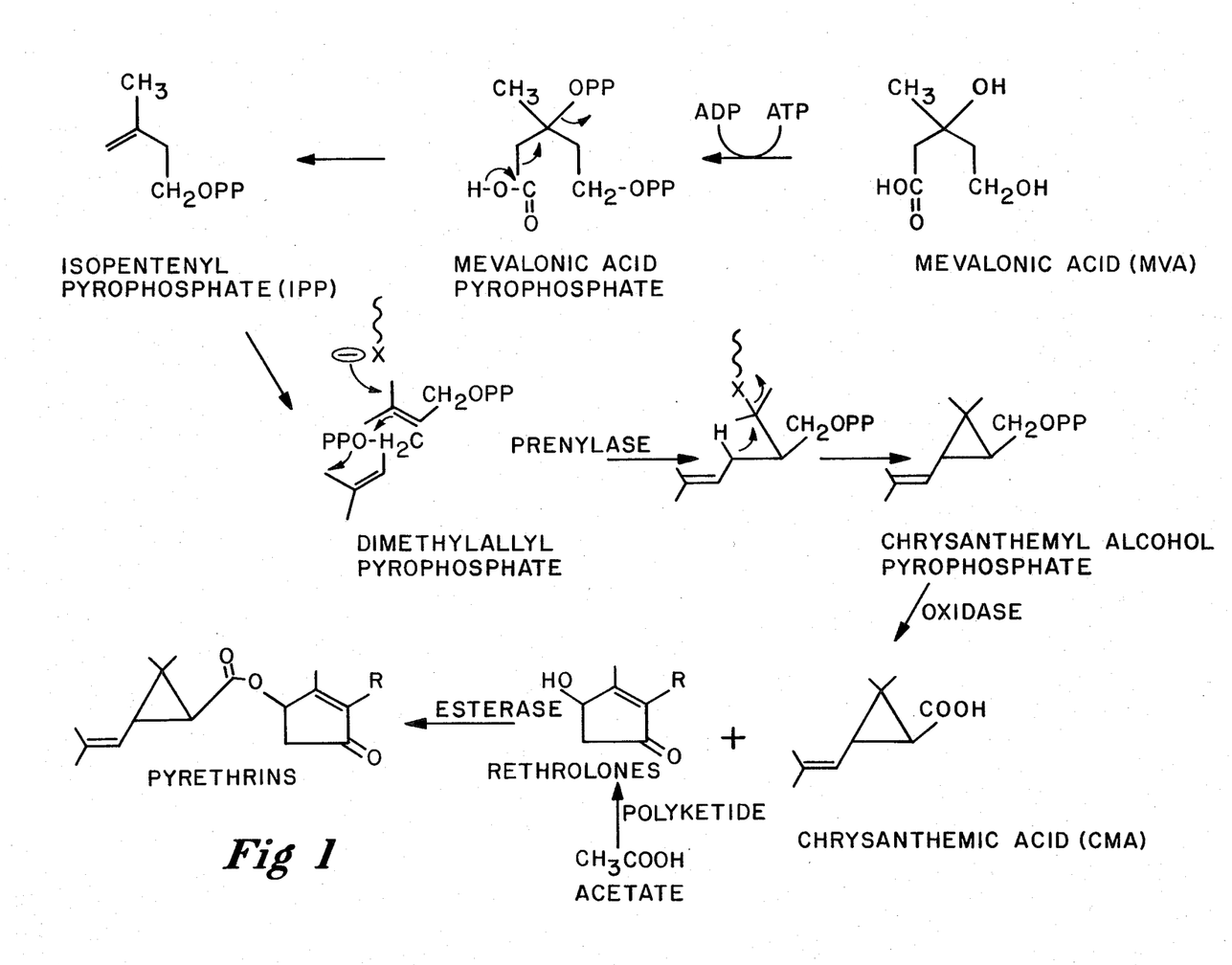
FIG. 1 shows in broad sweep the pyrethrin pathway of *Chrysanthemum cinerariaefolium* (Trev.) Bocc.

The above preferred embodiment stabilizing solution yields the highest bioactivity of the pyrethrin pathway shown in FIG. 1. Significant bioactivity of this pathway, however, is present where plant material is mixed with a hydrogen bonding inhibitor and ground in the presence of a stabilizing solution comprising a buffer with a pH in the range of about 6–8.5 and a thiol-reducing agent.

3. Biosynthesis of Pyrethrins

Pyrethrins may be synthesized by preparing a cell free homogenate containing bioactive enzyme(s) and cofactor(s) of the pyrethrin pathway shown in FIG. 1 and incubating the cell free homogenate and mevalonic acid or isopentenyl pyrophosphate. Labeled pyrethrins may be biosynthesized from such a cell free homogenate by using labeled mevalonic acid or labeled isopentenyl pyrophosphate.

Figure 2:
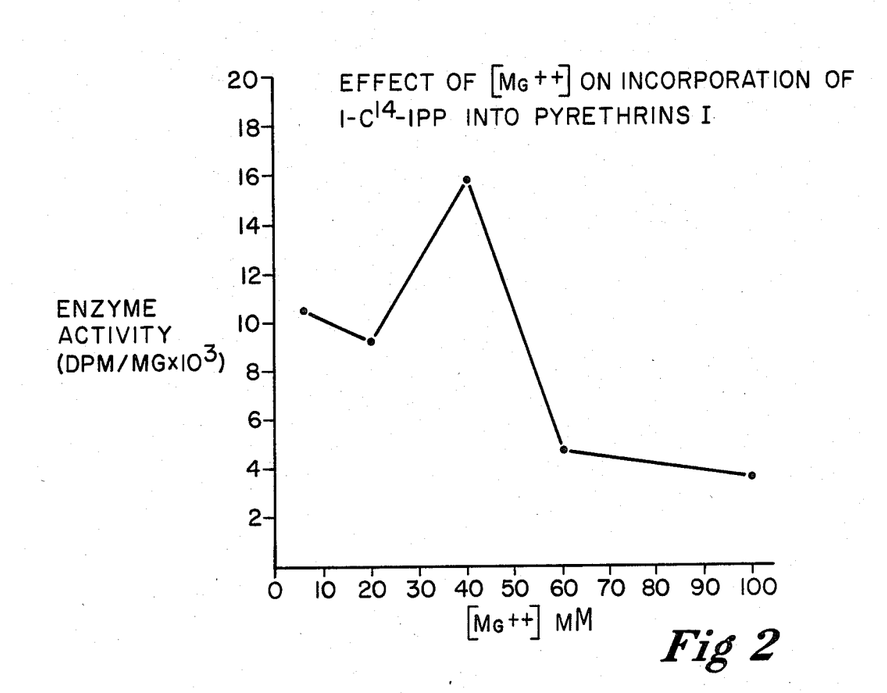
FIG. 2 shows the effect of $MG^{++}$ on incorporation of $1-C^{14}$-isopentenyl pyrophosphate into labeled pyrethrins.
Figure 3:
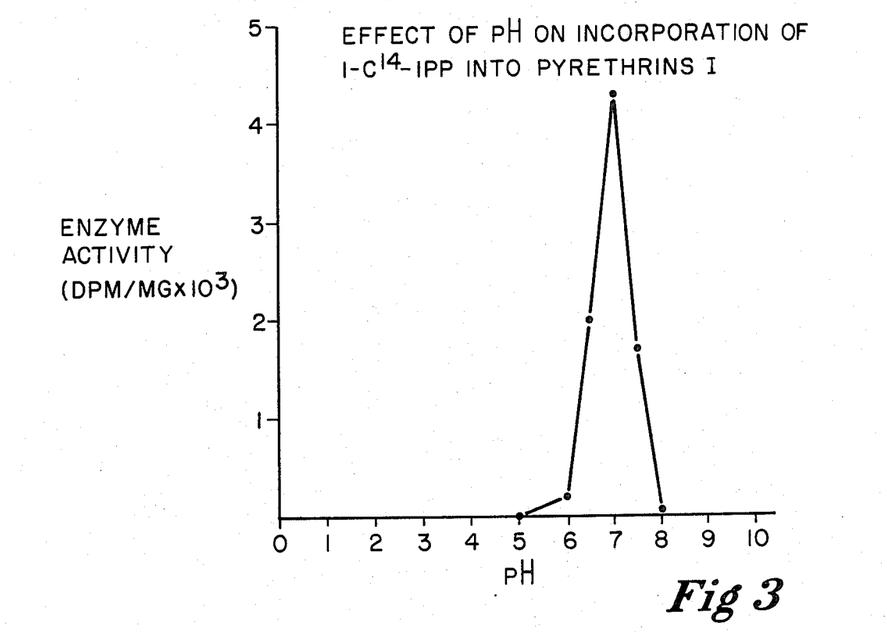
FIG. 3 shows the effect of pH on incorporation of $1-C^{14}$-isopentenyl pyrophosphate into labeled pyrethrins.

A cell free homogenate prepared according to the preferred embodiment set forth above can be used for the biosynthesis of pyrethrins. The biosynthesis of pyrethrins may be optimized, however, by adding a magnesium salt to the stabilizing solution used in preparing the cell free homogenate. FIG. 2 shows that the biosynthesis of pyrethrins from isopentenyl pyrophosphate is optimal within the range of about 10–50 mmole $MgCl_2$ in 5 ml of stabilizing solution used per gram of plant material. This is equivalent to a range of about $5-25\times10^{-2}$ mmole of $MgCl_2$ per gram of plant material. FIG. 3 shows that the biosynthesis of pyrethrins will be optimal where the stabilizing solution is buffered to a pH in the range of about 6–8.

The preferred biosynthesis of pyrethrins follows. A cell free homogenate was prepared according to the foregoing preferred embodiment and optimal pH range and $MgCl_2$ concentration. Cell free homogenates prepared in this manner typically contain 0.5–1.0 mg/ml of protein as determined by the Bradford method. Protein concentrations may be brought within this range by suitable departures from the 5 ml volume of stabilizing solution typically used.

Figure 10:
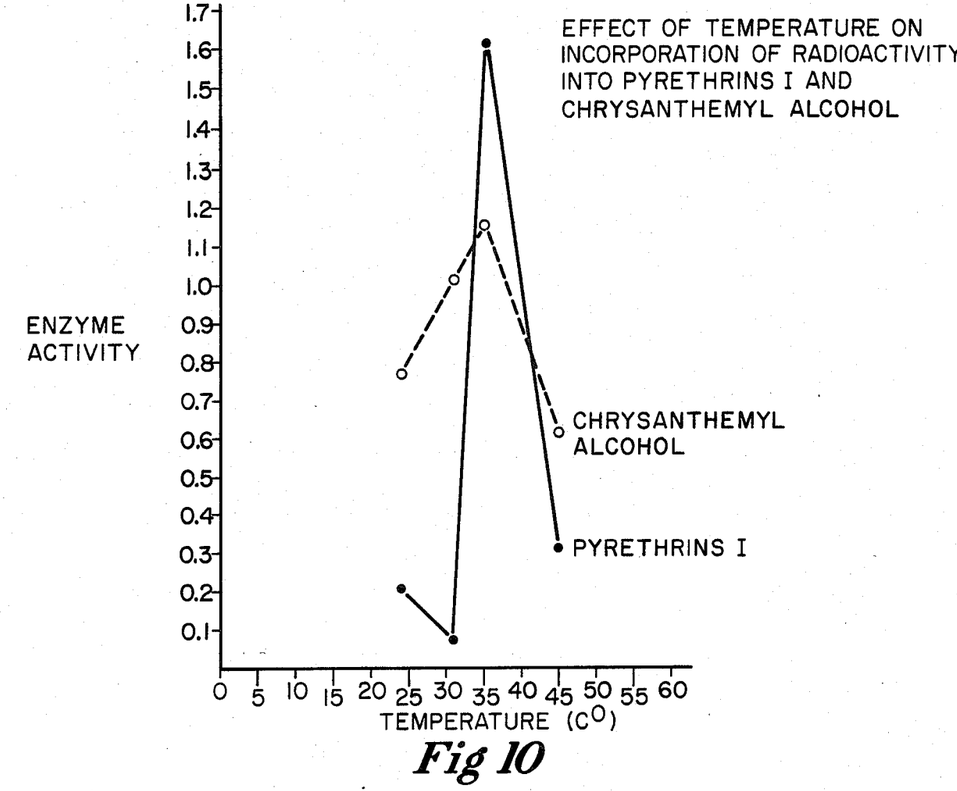
FIG. 10 shows the effect of temperature on incoporation of $1-C^{14}$-isopentenyl pyrophosphate into labeled pyrethrins I and chrysanthemyl alcohol.

0.2 $\mu$Ci of 1-$C^{14}$-isopentenyl pyrophosphate ammonium salt having a specific activity of 53 mCi/mmole (i.e. 177 mCi/mg), available commercially from Amersham Corp., Arlington Heights, Ill. 60005, were added to a volume in the range of about 0.5–3.0 ml, but preferably 1.0 ml, of cell free homogenate containing 0.5–1.0 mg/ml protein. This mixture was incubated preferably at 35° C., or alternatively as shown in FIG. 10 in the range of about 20°–40° C., for 18±2 hours. The incubate was boiled in order to denature the proteins contained therein.

In the alternative, 1.0 $\mu$Ci of 2-$C^{14}$-mevalonic acid having a specific activity of 53 mCi/mmole, available commercially from Amersham Corp., supra, were added to a volume in the range of about 0.5–3.0 ml, but preferably 1.0 ml, of cell free homogenate containing 0.5–1.0 mg/ml protein. To this 5 mmoles of ATP are added. This mixture was incubated preferably at 35° C., or alternatively in the range of about 20°–40° C., for 18±2 hours. The incubate was boiled in order to denature the proteins contained therein.

Figure 4:
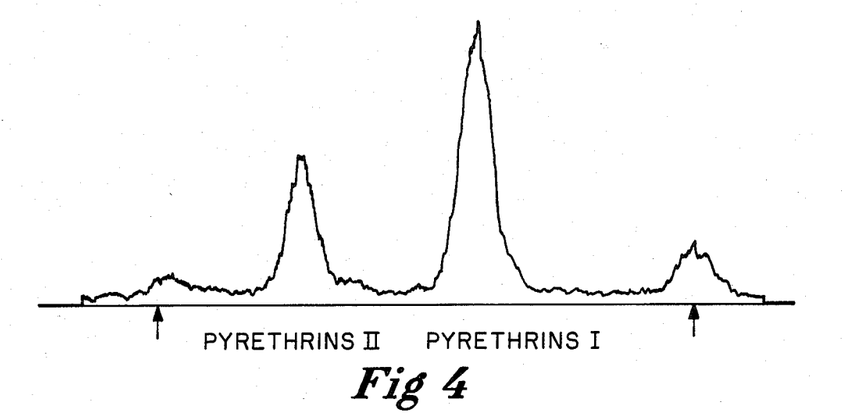
FIG. 4 shows a radioactivity scan of Silica gel GF plate of petroleum ether extract of labeled pyrethrins biosynthesized from $1-C^{14}$-isopentenyl pyrophosphate.
Figure 9:
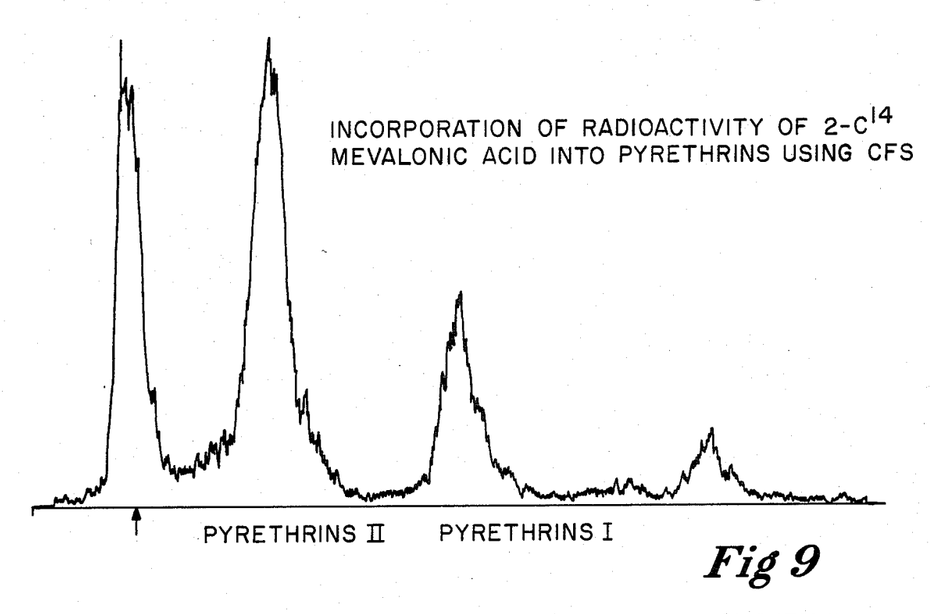
FIG. 9 shows a radioactivity scan of Silica gel GF plate of petroleum ether extract of labeled pyrethrins biosynthesized from $2-C^{14}$-mevalonic acid.

The boiled incubate, obtained from either the mevalonic acid or isopentenyl pyrophosphate incubation, was extracted with 3 washes of 10 ml of pesticide grade petroleum ether. The combined 3 washes of petroleum ether were dried over anhydrous sodium sulfate, decanted and evaporated to dryness on a rotovap at 40° C. The residue was dissolved in 0.25 ml of chloroform. The chloroform solution was chromatographed on a 20×20 cm Silica gel GF analytical plate developed with petroleum ether: ethyl acetate (9:1) to a height of at least 10 cm. The band corresponding to pyrethrins I, such as shown in FIG. 4 for incorporation of 1-$C^{14}$-isopentenyl pyrophosphate and in FIG. 9 for incorporation of 2-$C^{14}$-mevalonic acid, was scraped and its radioactivity was counted using a scintillation counter. The amount of radioactivity in disintigrations per minute (dpm) in the pyrethrins I is divided by the amount of protein in the cell free homogenate to yield the enzyme activity of the pathway. Typical results from using 2–3 gms of flower buds are:

| Amount of Protein: | 0.6 mg/ml |
| Aqueous Counts: | $2.6 \times 10^5$ cpm |
| Petroleum Ether Counts | $8.8 \times 10^3$ cpm |
| Pyrethrins I: | $0.6 \times 10^3$ cpm at 48% efficiency = $1.2 \times 10^3$ dpm |
| Enzyme Activity | $2 \times 10^3$ dpm/mg protein |

The specific activity of pyrethrins I was determined as follows. A cell free homogenate containing 0.6 mg/ml protein was incubated with 3.0 $\mu$Ci of 1-$C^{14}$-isopentenyl pyrophosphate for 18±2 hours. After boiling the incubate, it was extracted with pesticide grade petroleum ether as in the earlier example. The petroleum ether extract was evaporated to dryness and was dissolved in 0.25 ml of chloroform. 10 g of a standard containing 11% pyrethrins I and 9% pyrethrins II, the standard being available commercially as Premium Pyrocide 175 from McLaughlin Gormley King Co., Minneapolis, Minn. 55427, was added to the chloroform solution. The chloroform solution was then chromatographed on a 20×20 cm Silica gel GF analytical plate using petroleum ether: ethyl acetate (9:1) as developing solvent. The band corresponding to pyrethrins I was scraped and the compounds removed by washing with methanol several times. The methanol was evaporated to dryness on a rotovap at 40° C., and the residue was dissolved in 0.1 ml chloroform.

The chloroform solution was assayed for radioactivity and for pyrethrins I content. Using an Altex Si HPLC column with hexane: chloroform (3:2) containing 1% ethanol and a flow rate of 1.5 ml/min., a standard curve comparing $\mu$g of pyrethrin per peak area was prepared using Premium Pyrocide 175 solution containing 0.11 $\mu$g/$\mu$l pyrethrins I and 0.09 $\mu$g/$\mu$l pyrethrins II.

After assaying the chloroform solution for radioactivity and pyrethrins I content by HPLC (Si), the solution was purified by collecting the pyrethrins I as it eluted from the HPLC (Si) column. Pyrethrins I was again assayed and the radioactivity counted.

A further purification was accomplished using a reverse phase HPLC Altex-ODS (C-18) column with acetonitrile: water (80:20) mobile phase and flow rate of 1.5 ml/min. Pyrethrins I was assayed and the radioactivity counted as it eluted from the HPLC (C-18) column. The results are as follows:

| Administered Radioactivity | $1.94 \times 10^6$ cpm |
| Petroleum Ether Extract | $1.34 \times 10^5$ cpm |
| Pyrethrins I from Si Plate | $3.3 \times 10^3$ cpm |
| Specific Activity | $5.3 \times 10^4$ cpm/mg: |
| Pyrethrins I/PLC | $2.2 \times 10^7$ dpm/mmole |
| Specific Activity | $6.0 \times 10^4$ cpm/mg: |
| Pyrethrins I/HPLC (Si) | $2.5 \times 10^7$ dpm/mmole |
| Specific Activity | $5.8 \times 10^4$ cpm/mg: |
| Pyrethrins I/HPLC (C-18) | $2.4 \times 10^7$ dpm/mmole |

4. Biosynthesis of Chrysanthemyl Alcohol

Chrysanthemyl alcohol may be biosynthesized by incubating mevalonic acid or isopentenyl pyrophosphate and a cell free homogenate prepared according to the preferred embodiment method set forth above. After incubation, proteins are denatured by boiling and pyrethrins and other free terpenes contained in the incubate are extracted. The pH of the residue of the extraction is raised to about 9 and the residue is again incubated in the presence of a hydrolyzing agent such as an excess (1 mg) of alkaline phosphatase.

Figure 5:
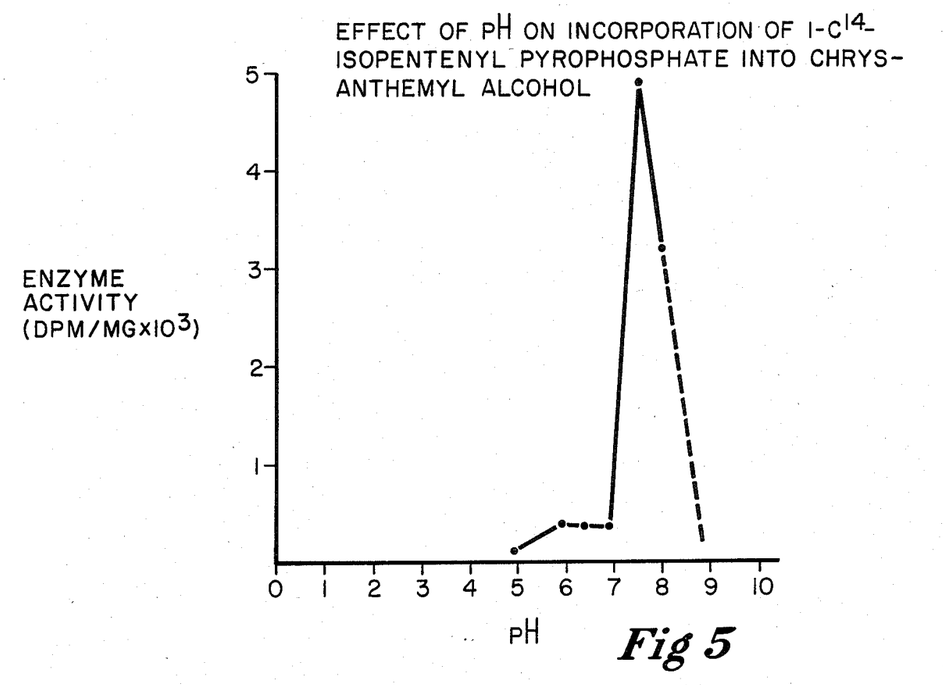
FIG. 5 shows the effect of pH on incorporation of $1-C^{14}$-isopentenyl pyrophosphate into labeled chrysanthemyl alcohol.
Figure 6:
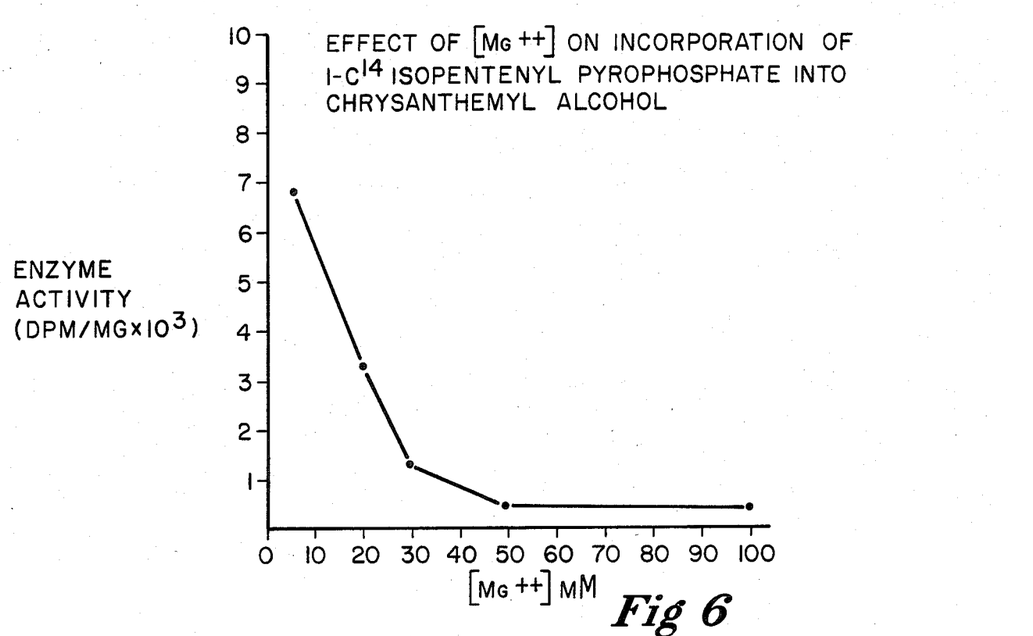
FIG. 6 shows the effect of $Mg^{++}$ on incorporation of $1-C^{14}$-isopentenyl pyrophosphate into labeled chrysanthemyl alcohol.

As shown in FIG. 5, biosynthesis of chrysanthemyl alcohol is optimized where the buffer maintains the pH of the stabilizing solution in the range of about 7–8.5. The biosynthesis of chrysanthemyl alcohol is further optimized by excluding magnesium salts from the stabilizing solution as shown in FIG. 6.

The biosynthesis of chrysanthemyl alcohol is illustrated by the following. As in the case of the biosynthesis of pyrethrin, 3.0 μCi of 53 mCi/mmole of 1-$C^{14}$-isopentenyl pyrophosphate was added to 2.5 ml of cell free homogenate containing 0.5–1.0 mg/ml of protein. After incubation at room temperature or about 20°–30° C. for 18±2 hours, the incubate was boiled to denature the protein. As set forth above, the incubate was washed with pesticide grade petroleum ether, thereby extracting pyrethrin and other free terpenes. 0.1M KOH was added in sufficient quantity to raise the pH of the residue to about 9. 1 mg of alkaline phosphatase was then added, followed by 18±2 hours of incubation at room temperature or within the range of about 20°–30° C. A volume equal to that of the incubate of 10% KOH is added to the incubate to stop the incubation. An extract consisting of 3 washes of 10 ml of pesticide grade petroleum ether is dried over anhydrous sodium sulfate, decanted and evaporated to dryness on a rotovap at 40° C. The residue is dissolved in 0.25 ml of chloroform.

Figure 7:
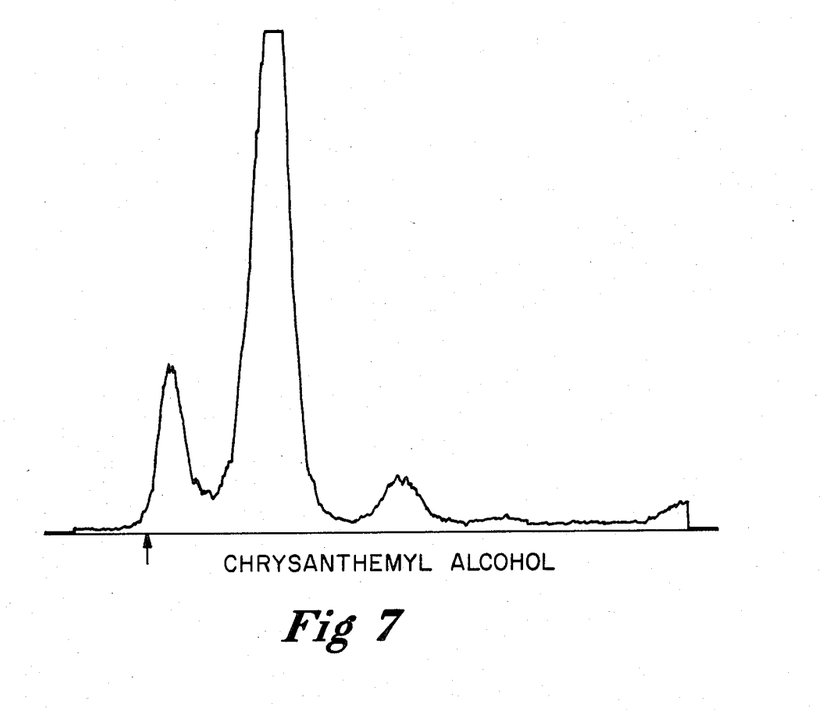
FIG. 7 shows a radioactivity scan of Silica gel GF plate of petroleum ether extract of labeled chrysanthemyl alcohol biosynthesized from $1-C^{14}$-isopentenyl pyrophosphate.
Figure 8:
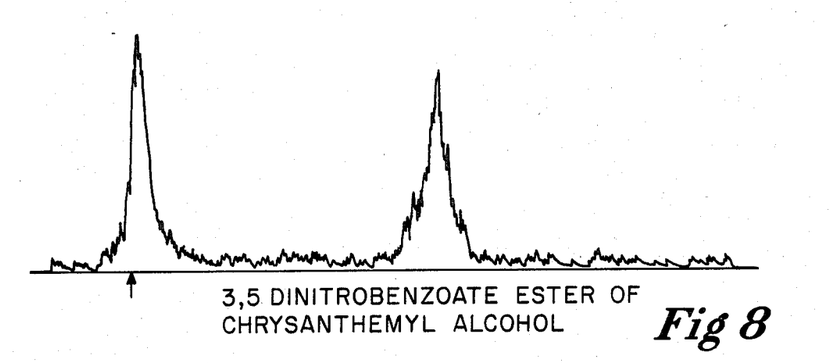
FIG. 8 shows a radioactivity scan of Silica gel GF plate of chloroform extract of labeled 3,5 dinitrobenzoate ester of chrysanthemyl alcohol.

The chloroform solution is chromatographed on a 20×20 cm Silica gel GF analytical plate developing with petroleum ether: ethyl acetate (8:2) to a height of at least 10 cm. FIG. 7 shows the radioactivity representing labeled chrysanthemyl alcohol. The band corresponding to chrysanthemyl alcohol is scraped and the radioactivity is counted using a scintillation counter. The amount of radioactivity (dpm) in the chrysanthemyl alcohol divided by the amount of protein (mg) in the cell free homogenate is referred to as the enzyme activity. Typical results using a cell free homogenate prepared from flower buds and having 0.9 mg/ml of protein are:

| | |
|---|---|
| Administered Radioactivity | 5 × $10^6$ cpm |
| Petroleum Ether | 5.7 × $10^5$ cpm |
| Chrysanthemyl Alcohol | 2.2 × $10^5$ cpm |
| Enzyme Activity | 2.0 × $10^5$ dpm/mg |

5. Preparation of 3,5 Dinitrobenzoate of Chrysanthemyl Alcohol

The band corresponding to chrysanthemyl alcohol was scraped and eluted from the Silica gel GF analytical plate with methanol. 20 mg of unlabeled chrysanthemyl alcohol were added as a carrier to the eluate. The methanol was evaporated in vacuo at 40° C. and the residue was dissolved in 2 ml of dry pyridine and mixed with a 10-fold excess, or about 240 mg, of 3,5 dinitrobenzoyl chloride and 15 ml of 5% potassium bicarbonate. The mixture was heated on a steam bath for 1.5 hours, followed by extraction with 3×15 ml chloroform washes. The extract was washed twice with 30 ml of 0.5N HCl followed by two washes of 30 ml of water. The washed chloroform extract was dried over sodium sulfate and evaporated to dryness. The residue crystallized from 95% ethanol. The following results were obtained:

| | |
|---|---|
| Chloroform Extract | 1.6 × $10^5$ cpm |
| Recrystallization of 3,5 dinitrobenzoate of chrysanthemyl alcohol: | |
| 1st crystals | 3.8 × $10^5$ dpm/mmole |
| 2nd crystals | 7.2 × $10^4$ dpm/mmole |
| 3rd crystals | 7.0 × $10^4$ dpm/mmole |

6. Differential Centrifugation of Cell Free Homogenate

The following differential centrifugation scheme was used to isolate various subcellular fractions of a cell free homogenate containing labeled pyrethrin.

The results of the above differential centrifugation scheme are as follows:

| FRACTION | % ACTIVITY |
|---|---|
| RAW HOMOGENATE | 100 |
| 500 G SUPERNATANT | 130 |
| 2000 G SUPERNATANT | 140 |
| 2000 G PELLET (PROPLASTIDS) | 20 |
| 100,000 G SUPERNATANT (CYTOSOL) | 130 |
| 100,000 G PELLET (MITOCHONDRIA) | 0 |

The above results support the conclusion that the enzyme(s) and cofactor(s) of the pyrethrin pathway of *Chrysanthemum cinerariaefolium* (Trev.) Bocc. reside in its cytosol.

7. Preparation of Cell Free Matrix

A cell free matrix containing bioactive enzyme(s) and cofactor(s) of the pyrethrin pathway was prepared with calcium alginate. A cell free homogenate, prepared according to the foregoing methods, was concentrated by vacuum dialysis to 2.4 mg/ml. A mixture of 3 % sodium alginate (75 mg) and distilled water (1.0 ml) was prepared by heating the sodium alginate and water until the alginate dissolved and the mixture was allowed to cool. 1.5 ml of concentrated cell free homogenate (2.4 mg/ml) were suspended in the cooled sodium alginate-water mixture. Small beads (1–4 mm) were formed by dropping the suspension through 1.0 ml pipet into a solution of 5 mM $CaCl_2$. The beads were allowed to harden for 1.5 hours or more before being washed 3 times with distilled water. For storage, beads were placed in the hydrogen binding inhibitor and stabilizing solution set forth above.

The cell free matrix was added to a graduated test tube and hydrogen binding inhibitor and stabilizing solution were added in the ratios set forth above for cell free homogenate to bring the total volume in the test tube to 2–3 ml. 1 μCi of 1-$C^{14}$-isopentenyl pyrophosphate was added and the mixture was incubated and later boiled according to the method set forth for preparing the cell free homogenate. In the alternative, mevalonic acid or labeled mevalonic acid may be used for biosynthesis. The beads were then filtered off and washed once with distilled water. Both the beads and filtrate were analyzed for activity:

| Sample | Aqueous | Pet Ether | PYI | Enzyme Activity |
|---|---|---|---|---|
| control | $1.1 \times 10^5$ cpm | $2.3 \times 10^3$ cpm (2%) | $0.4 \times 10^3$ dpm | $0.2 \times 10^3$ dpm/mg |
| beads | $2.0 \times 10^7$ cpm | $1.4 \times 10^4$ cpm (0.1%) | $2.0 \times 10^3$ dpm | $0.6 \times 10^3$ dpm/mg |
| filtrate | | $5.0 \times 10^3$ cpm | $2.3 \times 10^3$ dpm | $0.6 \times 10^3$ dpm/mg |

Figure 11:
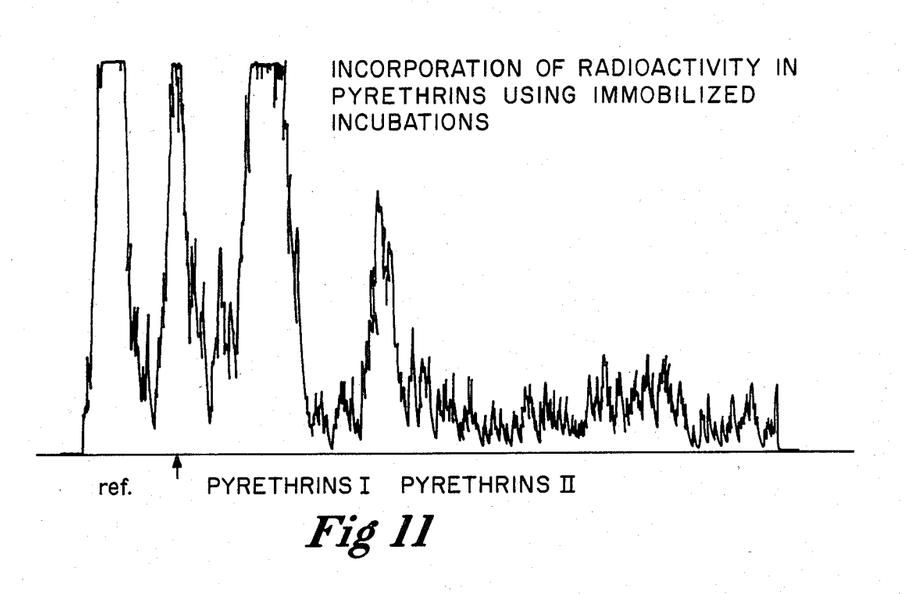
FIG. 11 shows a radioactivity scan of Silica gel GF plate of petroleum ether extract of labeled pyrethrins biosynthesized from $1-C^{14}$-isopentenyl pyrophosphate by a cell free matrix.

FIG. 11 shows a radioactivity scan of a petroleum ether extract, according to the method set forth for cell free homogenate biosynthesis, of labeled pyrethrins biosynthesized from the labeled isopentenyl pyrophosphate.

Figure 12:
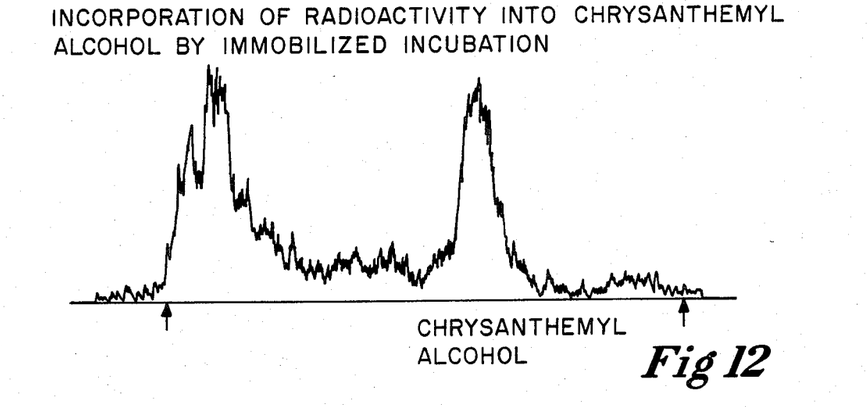
FIG. 12 shows a radioactivity scan of Silica gel GF plate of petroleum ether extract of labeled chrysanthemyl alcohol biosynthesized from $1-C^{14}$-isopentenyl pyrophosphate by a cell free matrix.

Labeled chrysanthemyl alcohol may be prepared from a cell free matrix according to the above preparation of the matrix and the further steps set forth for producing chrysanthemyl alcohol from the homogenate. FIG. 12 shows a radioactivity scan of a petroleum ether extract of labeled chrysanthemyl alcohol biosynthesized from labeled isopentenyl pyrophosphate.

8. Alternative Embodiments

From the foregoing, it will be obvious to those skilled in the art that various modifications in the above described methods can be made without departing from the spirit and scope of the invention. For example, isopentenyl pyrophosphate may be labeled with carbon 14 to form 1-$C^{14}$-isopentenyl pyrophosphate but may also be labeled at a carbon position elsewhere on the molecule. Furthermore, it is contemplated that isopentenyl pyrophosphate may be labeled other than by $C^{14}$ or tritium, and that such labeling will be incorporated in pyrethrins and chrysanthemyl alcohol by the pathway. Mevalonic acid may also be labeled in ways alternative to 2-$C^{14}$ labeling. It will also be obvious to those skilled in the art that methods of producing the cell free homogenate other than by mechanical disruption of cell wall/membranes will be possible. It will further be obvious to those skilled in the art that cell free homogenates may be prepared from pyrethrin producing Chrysanthemum species or Tagetes species of the family Compositae. Finally, but without limitation, chrysanthemyl alcohol pyrophosphate may be hydrolyzed by methods other than adding an alkaline phosphatase, and may be hydrolyzed with or without prior extraction of pyrethrins or free terpenes or denaturing of proteins. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing descriptions, and all changes which come within the meaning and range of equivalency of the claims are therefore intended to be embraced therein.

We claim:

1. A method for preparing a cell free homogenate containing bioactive enzyme(s) and cofactor(s) of the pyrethrin pathway of pyrethrin producing Chrysanthemum species or Tagetes species of the family Compositae which comprises homogenizing a mixture comprising:

plant material from pyrethrin producing Chrysanthemum species or Tagetes species of the family Compositae;

a hydrogen bonding inhibitor in an amount effective to competitively inhibit hydrogen bonding of the bioactive enzyme(s) and cofactor(s) by plant phenolics; and a stabilizing solution comprising a buffer with a pH in the range of about 6–8.5 and a thiol-reducing agent in an amount effective to competitively inhibit oxidation of bioactive enzyme(s) and cofactor(s) containing sulfhydryl groups and/or to competitively inhibit oxidation or covalent bonding of bioactive enzyme(s) and cofactor(s) by plant quinones.

2. The method of claim 1 wherein the Chrysanthemum species is *Chrysanthemum cinerarieafolium* (Trev.) Bocc.

3. The method of claim 1 wherein the hydrogen bonding inhibitor is a member of the group consisting of polyvinylpyrrolidone, nylon, carotene, collagen, polyamides, polyacrylamides, casein, arylhalides, and ethers.

4. The method of claim 3 wherein the hydrogen bonding inhibitor is polyvinylpyrrolidone and the effective amount of the polyvinylpyrrolidone is a mass about equal to the mass of the plant material.

5. The method of claim 1 wherein the thiol-reducing agent is a mercaptan.

6. The method of claim 5 wherein the mercaptan is a member of the group consisting of dithiothreitol, dithioerythirtol, glutathione or β-mercaptoethanol.

7. The method of claim 6 wherein the member is β-mercaptoethanol and the effective amount of β-mercaptoethanol is about 0.5 mmole β-mercaptoethanol per gram of plant material.

8. The method of claim 1 wherein the buffer is 2(N-morpholino) ethane sulfonic acid or 2(N-morpholino) propane sulfonic acid.

9. The method of claim 1 wherein the stabilizing solution further comprises an osmoticum in an amount effective to enhance the integrity of cell compartments.

10. The method of claim 9 wherein the osmoticum is sucrose and the effective amount is about 2.5 mmole sucrose per gram of plant material.

11. The method of claim 1 wherein the stabilizing solution further comprises an antioxidant in an amount effective to reduce oxidation of the bioactive enzyme(s) and cofactor(s).

12. The method of claim 11 wherein the antioxidant is sodium ascorbate and the effective amount is about 0.5 mmole sodium ascorbate per gram of plant material.

13. The method of claim 1 wherein the stabilizing solution further comprises a magnesium salt in an amount effective to enhance the conversion of mevalonic acid or isopentenyl pyrophosphate into pyrethrins.

14. The method of claim 13 wherein the magnesium salt is $MgCl_2$ and the effective amount is within the range of about $2.5-25 \times 10^2$ mmole per gram of plant material.

15. A method for the biosynthesis of pyrethrins or labeled pyrethrins comprising:

preparing a cell free homogenate containing bioactive enzyme(s) and cofactor(s) of the pyrethrin pathway of Chrysanthemum species and Tagetes species of the family Compositae; and adding together and incubating, until such pyrethrins or labeled pyrethrins are biosynthesized, the cell free homogenate and mevalonic acid or labeled mevalonic acid or isopentenyl pyrophosphate or labeled isopentenyl pyrophosphate.

16. The method of claim 15 wherein the Chrysanthemum species is *Chrysanthemum cinerariaefolium* (Trev.) Bocc.

17. The method of claim 15 wherein the preparation of the cell free homogenate comprises homogenizing a mixture comprising:
   plant material from pyrethrin producing Chrysanthemum species or Tagetes species of the family Compositae;
   a hydrogen bonding inhibitor in an amount effective to competitively inhibit hydrogen bonding of the bioactive enzyme(s) and cofactor(s) by plant phenolics; and
   a stabilizing solution comprising a buffer with a pH in the range of about 6-8 and a thiol-reducing agent in an amount effective to competitively inhibit oxidation of bioactive enzyme(s) and cofactor(s) containing sulfhydryl groups and/or to competitively inhibit oxidation or covalent bonding of bioactive enzyme(s) and cofactor(s) by plant quinones.

18. The method of claim 17 wherein the hydrogen bonding inhibitor is a member of the group consisting of polyvinylpyrrolidone, nylon, carotene, collagen, polyamides, polyacrylamides, casein, arylhalides, and ethers.

19. The method of claim 18 wherein the hydrogen bonding inhibitor is polyvinylpyrrolidone and the effective amount of the polyvinylpyrrolidone is a mass about equal to the mass of the plant material.

20. The method of claim 17 wherein the thiol-reducing agent is a mercaptan.

21. The method of claim 20 wherein the mercaptan is a member of the group consisting of dithiothreitol, dithioerythritol, glutathione, or $\beta$-mercaptoethanol.

22. The method of claim 21 wherein the member is $\beta$-mercaptoethanol and the effective amount of $\beta$-mercaptoethanol is about 0.5 mmole $\beta$-mercaptoethanol per gram of plant material.

23. The method of claim 17 wherein the buffer is 2(N-morpholino) ethane sulfonic acid or 2(N-morpholino) propane sulfonic acid.

24. The method of claim 17 wherein the stabilizing solution further comprises an osmoticum in an amount effective to enhance the integrity of cell compartments.

25. The method of claim 24 wherein the osmoticum is sucrose and the effective amount is about 2.5 mmole sucrose per gram of plant material.

26. The method of claim 17 wherein the stabilizing solution further comprises an antioxidant in an amount effective to reduce oxidation of the bioactive enzyme(s) and cofactor(s).

27. The method of claim 26 wherein the antioxidant is sodium ascorbate and the effective amount is about 0.5 mmole sodium ascorbate per gram of plant material.

28. The method of claim 17 wherein the stabilizing solution further comprises a magnesium salt in an amount effective to enhance the conversion of mevalonic acid or isopentenyl pyrophosphate into pyrethrins.

29. The method of claim 28 wherein the magnesium salt is $MgCl_2$ and the effective amount is within the range of about $2.5-25 \times 10^{-2}$ mmole per gram of plant material.

30. The method of claim 15 wherein the cell free homogenate and mevalonic acid or labeled mevalonic acid or isopentenyl pyrophosphate or labeled isopentenyl pyrophosphate are incubated at a temperature within the range of about 20°-40° C.

31. The method of claim 15 which further comprises denaturing proteins contained in the product of the incubation and extracting pyrethrins or labeled pyrethrins.

32. The method of claim 31 wherein the proteins contained in the product of the incubation are denatured by boiling the product.

33. The method of claim 15 wherein the labeled isopentenyl pyrophosphate is $1-C^{14}$-isopentenyl pyrophosphate or tritiated isopentenyl pyrophosphate.

34. The method of claim 15 wherein the labeled mevalonic acid is $2-C^{14}$-mevalonic acid or tritiated mevalonic acid.

35. A method for the biosynthesis of chrysanthemyl alcohol or labeled chrysanthemyl alcohol comprising:
   preparing a cell free homogenate containing bioactive enzyme(s) and cofactor(s) of the pyrethrin pathway of Chrysanthemum species or Tagetes species of the family Compositae;
   adding together and incubating the cell free homogenate and mevalonic acid or labeled mevalonic acid isopentenyl pyrophosphate or labeled isopentenyl pyrophosphate; and
   hydrolyzing chrysanthemyl alcohol pyrophosphate produced by the incubation.

36. The method of claim 35 wherein the Chrysanthemum species is *Chrysanthemum cinerariaefolium* (Trev.) Bocc.

37. The method of claim 35 wherein the preparation of the cell free homogenate comprises homogenizing a mixture comprising:
   plant material from pyrethrin producing Chrysanthemum species or Tagetes species of the family Compositae;
   a hydrogen bonding inhibitor in an amount effective to competitively inhibit hydrogen bonding of the bioactive enzyme(s) and cofactor(s) by plant phenolics; and
   a stabilizing solution comprising a buffer with a pH in the range of about 7-8.5 and a thiol-reducing agent in an amount effective to competitively inhibit oxidation of bioactive enzyme(s) and cofactor(s) containing sulfhydryl groups and/or to competitively inhibit oxidation or covalent bonding of bioactive enzyme(s) and cofactor(s) by plant quinones.

38. The method of claim 37 wherein the hydrogen bonding inhibitor is a member of the group consisting of polyvinylpyrrolidone, nylon, carotene, collagen, polyamides, polyacrylamides, casein, arylhalides, and ethers.

39. The method of claim 38 wherein the hydrogen bonding inhibitor is polyvinylpyrrolidone and the effective amount of the polyvinylpyrrolidone is a mass about equal to the mass of the plant material.

40. The method of claim 37 wherein the thiol-reducing agent is a mercaptan.

41. The method of claim 40 wherein the mercaptan is a member of the group consisting of dithiothreitol, dithioerythritol, glutathione, or $\beta$-mercaptoethanol.

42. The method of claim 41 wherein the member is $\beta$-mercaptoethanol and the effective amount of $\beta$-mercaptoethanol is about 0.5 mmole β-mercaptoethanol per gram of plant material.

43. The method of claim 37 wherein the buffer is 2(N-morpholino) ethane sulfonic acid or 2(N-morpholino) propane sulfonic acid.

44. The method of claim 37 wherein the stabilizing solution further comprises an osmoticum in an amount effective to enhance the integrity of cell compartments.

45. The method of claim 44 wherein the osmoticum is sucrose and the effective amount is about 2.5 mmole sucrose per gram of plant material.

46. The method of claim 37 wherein the stabilizing solution further comprises an antioxidant in an amount effective to reduce oxidation of the bioactive enzyme(s) and cofactor(s).

47. The method of claim 46 wherein the antioxidant is sodium ascorbate and the effective amount is about 0.5 mmole sodium ascorbate per gram of plant material.

48. The method of claim 35 wherein the cell free homogenate and mevalonic acid or labeled mevalonic acid or isopentenyl pyrophosphate or labeled isopentenyl pyrophosphate are incubated at a temperature within the range of about 20°-40° C.

49. The method of claim 35 wherein the chrysanthemyl alcohol pyrophosphate produced by the incubation is hydrolyzed by reacting the chrysanthemyl alcohol pyrophosphate with an alkaline phosphatase.

50. The method of claim 49 wherein the chrysanthemyl alcohol pyrophosphate is reacted with alkaline phosphatase at a pH of about 9.

51. The method of claim 35 wherein pyrethrins or labeled pyrethrins and other free terpenes are extracted prior to hydrolyzing the chrysanthemyl alcohol pyrophosphate.

52. The method of claim 35 wherein the labeled isopentenyl pyrophosphate is $1-C^{14}$-isopentenyl pyrophosphate or tritiated isopentenyl pyrophosphate.

53. The method of claim 35 wherein the labeled mevalonic acid is $2-C^{14}$-mevalonic acid or tritiated mevalonic acid.

54. A method for preparing a cell free matrix containing bioactive enzyme(s) and cofactor(s) of the pyrethrin pathway of pyrethrin producing Chrysanthemum species or Tagetes species of the family Compositae which comprises:
   preparing a cell free homogenate from plant material from pyrethrin producing Chrysanthemum species or Tagetes species of the family Compositae, said cell free homogenate containing enzyme(s) and cofactor(s) of the pyrethrum pathway; and
   immobilizing said enzyme(s) and cofactor(s) by a matrix.

55. The method of claim 54 wherein the Chrysanthemum species is *Chrysanthemum cinerariaefolium* (Trev.) Bocc.

56. The method of claim 54 wherein the matrix comprises calcium alginate.

57. A method for the biosynthesis of pyrethrins or labeled pyrethrins comprising:
   preparing a cell free matrix containing bioactive enzyme(s) and cofactor(s) of the pyrethrin pathway of Chrysanthemum species and Tagetes species of the family Compositae; and
   adding together and incubating the cell free matrix and mevalonic acid or labeled mevalonic acid or isopentenyl pyrophosphate or labeled isopentenyl pyrophosphate.

58. The method of claim 57 wherein the Chrysanthemum species is *Chrysanthemum cinerariaefolium* (Trev.) Bocc.

59. A method for the biosynthesis of chrysanthemyl alcohol or labeled chrysanthemyl alcohol comprising:
   preparing a cell free matrix containing bioactive enzyme(s) and cofactor(s) of the pyrethrin pathway of Chrysanthemum species or Tagetes species of the family Compositae;
   adding together and incubating the cell free homogenate and mevalonic acid or labeled mevalonic acid or isopentenyl pyrophosphate or labeled isopentenyl pyrophosphate; and
   hydrolizing chrysanthemyl alcohol pyrophosphate produced by the incubation.

60. The method of claim 59 wherein the Chrysanthemum species is *Chrysanthemum cinerariaefolium* (Trev.) Bocc.

* * * * *